United States Patent [19]

Kallianos et al.

[11] 4,091,823

[45] May 30, 1978

[54] CYCLOGERANIOL AND DERIVATIVES THEREOF AS TOBACCO FLAVORANTS

[75] Inventors: Andrew George Kallianos; Everett West Southwick, both of Durham, N.C.; Melvyn Irving Simpson, Fargo, N. Dak.

[73] Assignee: Liggett Group Inc., Durham, N.C.

[21] Appl. No.: 704,721

[22] Filed: Jul. 12, 1976

[51] Int. Cl.$^2$ .............................................. A24B 3/12
[52] U.S. Cl. ................................. 131/17 R; 131/144
[58] Field of Search ................. 131/17, 144, 2, 140 R, 131/140 C, 144; 252/522

[56] References Cited

PUBLICATIONS

Perfume and Flavor Chemicals, vol. 1, by Steffen Arctander, published by the author, 1969, Montclair, N.J. (U.S.A.).

*Primary Examiner*—Robert W. Michell
*Assistant Examiner*—V. Millin
*Attorney, Agent, or Firm*—Michael L. Hendershot; J. Bowen Ross, Jr.

[57] ABSTRACT

A process for improving, enhancing or modifying the organoleptic properties of tobacco products which comprises adding thereto a compound selected from the group of alpha-cyclogeraniol, beta-cyclogeraniol, and certain ether, ester, thiol and thioether derivatives thereof.

24 Claims, No Drawings

CYCLOGERANIOL AND DERIVATIVES THEREOF AS TOBACCO FLAVORANTS

The present invention relates to a tobacco product and has for an object the provision of a composition and process for improving, modifying or enhancing the flavor and aroma of tobacco smoke.

It is well known in the tobacco art that flavor and aroma of tobacco smoke are perhaps the most important considerations as far as the ultimate consumer is concerned. In the case of most smoking tobacco products manufactured today the desired flavor and aroma are achieved by the blending of domestic and oriental tobaccos each of which contributes its own characteristic aroma and flavor during smoking. However, the manufacturer may be restricted in achieving a desirable product because of limitations on the available types of tobacco with which he can work.

Accordingly, it is an object of the present invention to ameliorate the restrictive conditions inherent in blending by utilizing a new class of additive materials, which when applied to the tobacco product improves, modifies or enhances the flavor and aroma of the tobacco smoke emitted from these products thereby enhancing the pleasure derived by the consumer.

A further object of this invention is the provision of a process for enhancing or otherwise improving the flavor and aroma of certain domestic, oriental, reconstituted or synthetic tobaccos and blends thereof which may be deficient in said flavor or aroma.

An additional object of this invention is to provide a smoking product, such as cigarettes, cigars, or pipe tobacco, and a process for forming same whereby the flavor and aroma are enhanced during smoking.

Further and additional objects will appear from the following description and the appended claims.

In accordance with the practice of the present invention the flavor and aroma of tobacco smoke is improved by adding to the tobacco a flavouring composition containing at least one compound having one of the following formulas:

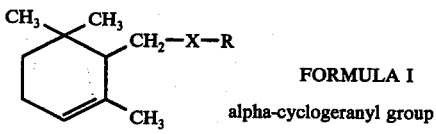

FORMULA I
alpha-cyclogeranyl group

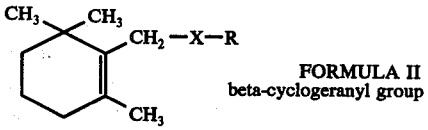

FORMULA II
beta-cyclogeranyl group wherein X is oxygen or sulfur and R is hydrogen; or a straight or branched chain alkyl group, having from 1 to 10 carbon atoms, preferably 1 to 6 carbon atoms, in the alkyl chain, such as methyl, ethyl, n-propyl, iso-propyl, n-butyl, hexyl, 2-ethylhexyl, octyl, decyl, and the like; or an aryl or aralkyl group such as phenyl, benzyl, betaphenylethyl and the like; or a cycloaliphatic group, including the monocyclic and bicyclic groups, such as cylopentyl, cyclohexyl, bicyclo-[2.2.1]-heptyl, and the like; or an acyl residue of an aliphatic or aromatic monocarboxylic acid, having from 1 to 9 carbon atoms in the acyl chain, such as the acyl residues of acetic, propionic, butyric, valeric, or benzoic acids, and the like. Preferably R in both Formulas I and II above is hydrogen or lower acyl.

All of the above compounds embraced by Formulas I and II above can be prepared by known techniques. Briefly, the preparation of alpha-cyclogeraniol is accomplished in a two step process. First, citral anil is cyclized by acid catalysis to form alpha-cyclocitral in modest yield. Second, the alpha-cyclocitral is reduced with sodium borohydride to produce alpha-cyclogeraniol. Treatment of the alpha-cyclocitral with alcoholic base and then reduction with sodium borohydride yields beta-cyclogeraniol. The beta- and alpha-cyclogeraniol compounds may also be obtained by degradation of appropriate precursors.

The etherification of alpha- or beta-cyclogeraniol can be effected by treatment of either or both compounds with sodium hydride and the appropriate alkyl iodide, e.g., beta-cyclogeraniol methyl ether is prepared by treatment of beta-cyclogeraniol with sodium hydride and methyl iodide.

Esterification of alpha- and/or beta-cyclogeraniol can be effected by conventional esterification techniques.

The thio ethers embraced by Formulas I and II above can be prepared by reaction of the alpha- and/or beta-cyclogeranyl bromide with the appropriate sodium thioalkylate e.g., beta-cyclogeranyl thiomethyl ether is prepared from beta-cyclogeranyl bromide by reaction with sodium thiomethylate.

The method of preparation of alpha-cyclogeraniol and its derivatives described herein yields a racemic mixture which has been found to be suitable for the practice of the present invention. One or both enantiomers of alpha-cyclogeraniol or its derivatives may be obtained either by synthesis in a chiral environment or by resolution of the racemate by any of the techniques which are available to effect such separations. In light of our experience with the racemate, it is felt that either of the optically active enantiomers would be suitable flavoring agents for tobacco and would be considered to fall within the purvue of this invention.

It will be readily apparent to those experienced in the art that the above methods of preparation are intended only to be illustrative and not exclusive and that the products may be obtained by other methods and from other precursors, both chemically and enzymatically.

In the practice of the present invention a compound or a mixture of compounds having a structural formula of Formula I or II above is added to tobacco or applied to a tobacco product or its component parts to modify or enhance the flavor thereof. The compounds of the present invention are especially useful as flavorants for cigarette tobacco. The quantity of flavorant employed is not narrowly critical and can vary over a wide range. Normally the flavorant is added in an amount to give a final concentration of from about 0.0001 to about 0.1 weight percent, preferably from about 0.001 to about 0.01 weight percent based on the weight of the tobacco or the tobacco product. However, the amount used will depend upon the amount or particular type of flavor desired and the particular compound or mixture thereof that is used.

The flavoring agents of the present invention may be incorporated at any step in the processing of tobacco. They may be applied to the individual tobacco blend components, such as the natural tobaccos, reconstituted tobacco sheet, or tobacco substitutes of natural or synthetic origin. Preferably the additive is added after aging, curing and shredding and before the tobacco is formed into cigarettes.

Furthermore, the flavoring agents of this invention may be blended with the tobacco in any convenient manner. For example, they can be dissolved in ethanol or any other suitable solvents, or admixed with a carrier such as casing solution to form a suspension or dispersion, and the resulting combination sprayed, dipped or otherwise applied on the tobacco. Thus water or volatile organic solvents, such as alcohol; glycols for instance propylene glycol; ether; acetone; volatile hydrocarbons; mixtures thereof and the like, may be used as the carrier medium for the agent while it is applied to the tobacco. Alternatively, the agent or mixtures thereof can be blended with other additives and then mixed into the tobacco. Thus it can be incorporated into blends normally employed to produce reconstituted tobacco sheet or tobacco substitutes of natural or synthetic origin. Inasmuch as the flavoring agents of this invention are volatile, they may also be incorporated into the filter tip, the seam paste employed for gluing the cigarette paper or the packaging material.

While this invention is principally useful in the manufacture of cigarette tobacco, it is also suitable for use in connection with the manufacture of pipe tobacco, cigars or other tobacco products. The term "tobacco" as used throughout this specification is meant any composition intended for use by smoking or otherwise, whether composed of tobacco plant parts or substitute materials or both.

Some of the tobacco additives of this invention have found particular utility when incorporated in those smoking tobaccos which normally exhibit a harsh taste on smoking. The incorporation of the additives of the present invention in these tobaccos results in a much smoother smoke, mouth-wetting effects and usually a pleasant aftertaste. The monocarboxylic acid esters of alpha- and beta-cyclogeraniol, particularly the acetate, have the most pronounced effect of the flavorants of this invention in overcoming the harsh taste that results from certain smoking compositions. This effect and others will become more apparent from the examples which follow.

The following examples are merely illustrative and are not presented as a definition of the limits of the invention.

In all of the following examples when the concentration of the additive is given in units of ppm, it has been calculated on a weight basis.

EXAMPLE 1

Beta-cycloheraniol 7.1 grams (g) of beta-cyclocitral was added dropwise to a suspension of 1.8 g of sodium borohydride in 50 milliliters (ml) of 95% ethanol cooled in an ice bath. When the addition was complete, the ice bath was removed and water was added to dissolve any remaining solids. The reaction mixture was then stirred overnight at room temperature. The solvent was removed at reduced pressure and the residue taken up in ether and then sequentially washed with 1 normal acetic acid, dilute aqueous sodium bicarbonate and finally water. The ether extract was dried over sodium sulfate, filtered and concentrated to give 7.5 g of a colorless oil which was distilled to give a quantitative yield of beta-cyclogeraniol, boiling point (bp) 54°–55° C/0.5 millimeters (mm); 102° C/30 mm. The correct structural assignment was confirmed by the following spectroscopic data:

Infra-red (IR) in $CCl_4$: 3650, 1654 and 980 cm$^{-1}$
Proton Magnetic Resonance (NMR) in $CCl_4$:

| | |
|---|---|
| 4.13 (s,2H) | —$CH_2OH$ |
| 1.75 (s,3H) | =C—$CH_3$ |
| 1.08 (s,6H) | (—$CH_3$)$_2$ |
| 1.4–2.2 (broad) | ring methylenes |

Mass Spectrum: m/e 154 (M$^+$), 139, 123, 121

The beta-cyclocitral used to prepare the beta-cyclogeraniol, above, was prepared according to the method described by R. N. Gedge et. al., Can. J. Chem. 49, 1764 (1971). The disclosure of which is incorporated herein by reference. The product was isolated by steam distillation at reduced pressure and by this technique was sufficiently pure for use as a starting material without additional purification.

An ethanolic solution of the compound prepared as described in this Example was applied to a commerical blend of cigarette tobaccos in an amount sufficient to provide tobacco containing approximately 0.0025 percent by weight of the additive on a dry basis. The tobacco was then manufactured into cigarettes by the usual techniques. Upon flavor evaluation, a panel of experts found the cigarette to produce a smoke that was smoother and sweeter than that from an untreated control cigarette.

Sample cigarettes prepared in the same manner as described above and containing the additive compound at a level of 0.01 percent by weight were judged to produce a smoother smoke and "mouth-wetting" properties with a pleasant aftertaste.

In this and subsequent examples the control cigarette was identical in all respects to the sample cigarette with the exception that it did not contain the additive.

EXAMPLE 2

Beta-cyclogeraniol methyl ether

To a suspension of 1.26 g sodium hydride in 25 ml. dimethoxyethane (DME) was added dropwise with magnetic stirring a solution of 4.59 g beta-cyclogeraniol, in 20 ml DME. The beta-cyclogeraniol was prepared according to the method of Example 1. The suspension was stirred vigorously for 1 hr. at room temperature. Then a solution of 4.65 g methyl iodide in 20 ml. DME was added dropwise and the resulting suspension was heated under reflux overnight. The reaction mixture was cooled to room temperature, filtered and concentrated to a brown oil. Distillation of the oil through a spinning-band column gave beta-cyclogeraniol methyl ether, b.p. 70° C/35 mm.

The correct structural assignment was confirmed by the following spectroscopic data:

Infra-red ($CCl_4$): 1660, 1090, 945 cm$^{-1}$
Proton Magnetic Resonance ($CCl_4$):

| | | |
|---|---|---|
| 3.65 | (s,2H) | —$CH_2O$ |
| 3.10 | (s,3H) | —$OCH_3$ |
| 1.52 | (s,3H) | =C—$CH_3$ |
| 0.90 | (s,6H) | $\diagup$ $CH_3$ $\diagdown$ $CH_3$ |

| | | |
|---|---|---|
| 1.2–2.0 (broad) ring methylenes | | |

Mass Spectrum: M/e 168 (M+), 136, 123, 121, 93

The aroma of the compound prepared as described in this Example has been described by a panel of experts as reminiscent of menthol and camphor with woody, terpene-like notes.

Upon application of this compound to a commercial blend of cigarette tobaccos by the same method and procedure described in Example I, at a level of 25 ppm, a panel of experts found the cigarette smoke to be smoother than an untreated control cigarette and possessed a slight minty character.

EXAMPLE 3

Beta-cyclogeraniol n-butyl ether 3.7 g of beta-cyclogeraniol, prepared according to the method in Example I, was dissolved in 20 ml. of dimethoxyethane (DME) and added dropwise with stirring to a suspension of 0.58 g sodium hydride in 25 ml DME. The suspension was stirred vigorously for 1 hr. at room temperature. Then a solution of 3.62 g n-butyl bromide in 20 ml DME was added dropwise and the resulting suspension was heated under reflux overnight. The reaction mixture was cooled to room temperature, filtered and concentrated to a brown oil. Distillation of the oil through a spinning band column gave beta-cyclogeraniol n-butyl ether, bp 110°–125° C/30 mm.

The correct structural assignment was confirmed by the following spectroscopic data:

Infra-red ($CCl_4$): 1655, 1090 $cm^{-1}$
Proton Magnetic Resonance ($CCl_4$):

| 3.75 | (s, 2H) | $-CH_2O-$ |
|---|---|---|
| 3.25 | (t, 2H) | $-OCH_2-$ |
| 1.6 | (s, 3H) | $=C-CH_3$ |
| 0.95 | (s, 6H) | $\begin{matrix} CH_3 \\ \diagup \\ \diagdown \\ CH_3 \end{matrix}$ |
| 0.8–2.0 (broad) methylene protons | | |

Mass Spectrum: m/e 210 (M+), 136, 123, 121, 93

Upon application of this compound to a commercial blend of cigarette tobaccos, as described in Example I, at a level of 50 ppm, a panel of flavor experts found the cigarette smoke to be smoother and more bland than an untreated control cigarette.

EXAMPLE 4

Beta-cyclogeraniol n-hexyl ether

To a solution of 3.85 g beta-cyclogeraniol in 25 ml. dimethoxyethane was added by syringe 12 ml. of a 2.3 M solution of methyl lithium in ether. The reaction mixture was stirred for 1 hr. at room temperature and then a solution of 4.1 g 1-bromohexane in 10 ml. dimethoxyethane was added dropwise. The reaction mixture was heated under reflux for 48 hrs. and then cooled in a stream of nitrogen. To the gummy residue was added 50 ml. $H_2O$ and 50 ml. ether. The layers were separated and the aqueous layer extracted with ether (3 × 50 ml.). The combined extracts were dried over $MgSO_4$ and concentrated to give a light yellow oil. The oil was chromatographed on alumina (eluted with benzene) to remove residual alcohol and then distilled at reduced pressure to give beta-cyclogeraniol n-hexyl ether, bp, 74°–76° C/0.1 mm.

The correct structural assignment was confirmed by the following spectroscopic data:

Infra-red ($CCl_4$): 1650, 1092 $cm^{-1}$
Proton Magnetic Resonance ($CCl_4$)

| 3.75 | (s, 2H) | $-CH_2O-$ |
|---|---|---|
| 3.22 | (t, 2H) | $-O-CH_2-$ |
| 1.6 | (s, 3H) | $=C-CH_3$ |
| 0.95 | (s, 6H) |  |
| 0.8–2.0 (broad) methylene protons | | |

Mass Spectrum: m/e 238 (M+), 136, 123, 121, 93

Upon application of the compound prepared as described in this Example to a commercial blend of cigarette tobaccos at a level of 50 ppm, a panel of experts found the smoke to be more bitter and peppery than an untreated control cigarette.

EXAMPLE 5

Beta-cyclogeraniol isopropyl ether

First, the starting material, beta-cyclogeranyl bromide, was prepared according to the method described by R. Kuhn and M. Hoffer in CHEM. BER., 67B, 357 (1934); the disclosure of which is incorporated herein by reference. This method involved the addition of 4 drops of pyridine to a cold (0° C.) solution of 5 g of beta-cyclogeraniol dissolved in 10 ml. of petroleum ether. To this solution was added 3.6 g phosphorus tribromide. After stirring for 2 hrs. at 0° C, the mixture was treated with $H_2O$, the layers separated and the organic layer washed several times with a saturated $NaHCO_3$ solution. The organic layer was dried over $CaCl_2$ and concentrated to give an oil which was used without further purification.

The crude bromide obtained as described above was dissolved in 50 ml isopropyl alcohol and added dropwise to a warm solution of sodium isopropoxide prepared from 2.3 g Na and 100 ml. isopropyl alcohol. The resulting suspension was heated under reflux overnight, filtered while warm and diluted with an equal volume of water. The aqueous solution was concentrated at reduced pressure to ⅓ volume. The residue was extracted with ether (3 × 50 ml.) and the extracts dried over $MgSO_4$. After concentration of the extracts at reduced pressure the residual oil was chromatographed on alumina (petroleum ether: benzene eluent) to remove residual alcohol. The material obtained from the column was distilled to give beta-cyclogeraniol isopropyl ether, bp 46°/0.05 mm.

The correct structural assignment was confirmed by the following spectroscopic data:

Infra-red ($CCl_4$): 1655, 1145, 1125, 1045 $cm^{-1}$
Proton Magnetic Resonance ($CCl_4$):

| 3.75 | (s, 2H) | $-CH_2-O$ |
|---|---|---|
| 3.45 | (septet, 1H, J=6$H_3$) | $O-CH(CH_3)_2$ |
| 1.6 | (s, 3H)=$CH_3$ | |
| 1.1 | (d, 6H, J=6$H_3$) | $CH(CH_3)_2$ |

| | | |
|---|---|---|
| 0.95 | (s, 6H) | CH₃ \ / CH₃ (gem-dimethyl) |
| 1.0–2.0 (broad) methylene protons | | |

Mass Spectrum: m/e 196 (M⁺), 139, 136, 121, 98

Upon application of the compound prepared as described in this Example to a commercial blend of cigarette tobaccos at a level of 50 ppm, a panel of experts found the cigarette smoke to be smoother with increased body and amplitude compared to an untreated control cigarette.

EXAMPLE 6

Beta-cyclogeranyl acetate

To a solution of 3.9 g beta-cyclogeraniol, prepared as described in Example I, in 50 ml. anhydrous ether cooled to 0° C. was added dropwise 5.25 g triethylamine followed by 2.0 g acetyl chloride. The reaction mixture was allowed to warm to room temperature and stirred overnight. Water was added until the triethylamine hydrochloride was dissolved, the organic layer separated, and the aqueous layer extracted twice with 50 ml. ether. The combined ether extracts were extracted once with 50 ml. 3N HCl, once with water and dried over MgSO₄. After filtering, the organic extract was concentrated to give 5.7 g of orange oil. The oil was distilled through a spinning-band column to give beta-cyclogeranyl acetate, bp 70°–72°/1.7 mm. Beilstein reports beta-cyclogeranyl acetate as having bp 130°–132°/30 mm.

The correct structural assignment was confirmed by the following spectroscopic data:

Infra-red (CCl₄): 1735, 1230, 1020 cm⁻¹
Proton Magnetic Resonance (CCl₄):

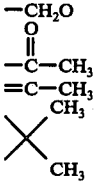

Mass Spectrum: m/e 196 (M⁺), 136, 121, 93, 79, 43

The aroma of the compound prepared as described in Example 6 has been described by a panel of experts as being cedar-woody, floral and oily.

Upon application of the compound prepared as described in this Example to a commercial blend of cigarette tobaccos, at a level of 50 ppm, a panel of experts found the cigarette smoke to be smoother and more bland than an untreated control cigarette.

EXAMPLE 7

Beta-cyclogeranyl propionate

To a solution of 2.9 g propionyl chloride in 30 ml benzene was added dropwise with stirring a mixture of 5.0 g beta-cyclogeraniol, prepared as described in Example 1, and 7.2 g N,N-diethylaniline in 30 ml. benzene. The reaction mixture was stirred overnight at room temperature and then diluted with 50 ml. of water. The aqueous layer was drawn off and extracted twice with 30 ml. benzene. The combined organic layers were extracted once with 50 ml. 3N HCl, twice with 50 ml. saturated aqueous NaHCO₃ and once with 50 ml. H₂O. The organic layer was dried over MgSO₄, filtered and concentrated at reduced pressure to give an oil. Distillation of the oil gave beta-cyclogeranyl propionate, bp 64°/0.15 mm.

The correct structure assignment was confirmed by the following spectroscopic data:

Infra-red (CCl₄): 1730, 1180 cm⁻¹
Proton Magnetic Resonance (CCl₄):

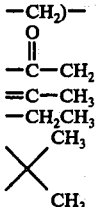

Mass Spectrum: m/e 210 (M⁺), 137, 121, 107, 93, 56

The aroma of the compound prepared as described in Example 7 has been described by a panel of experts as resembling camphor with a sweet, orange character.

EXAMPLE 8

Beta-cyclogeranyl n-valerate

To a solution of 8.0 g n-valeryl chloride in 30 ml. benzene was added dropwise with stirring a mixture of 5 g beta-cyclogeraniol and 7.1 g triethylamine in 30 ml benzene. The resulting suspension was stirred overnight at room temperature. To the suspension was added slowly a quantity of water sufficient to dissolve the solids. The layers were then separated and the organic layer was dried over MgSO₄ and concentrated at reduced pressure. The residual oil was distilled to give 1.6 g of beta-cyclogeranyl n-valerate, bp 78°–85° C./0.15 mm.

The correct structural assignment was confirmed by the following spectroscopic data:

Infra-red (CCl₄); 1727, 1170 cm⁻¹
Proton Magnetic Resonance (CCl₄):

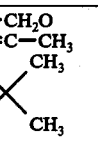

Mass Spectrum: m/e 238 (M⁺), 136, 121, 107, 93

Upon application of the compound prepared as described in this Example to a blend of cigarette tobaccos at a level of 50 ppm, a panel of experts found the cigarette smoke to have a fermented fruit taste that was not detected in the untreated control cigarette.

EXAMPLE 9

Beta-cyclogeranyl 3-methylvalerate

To a solution of 4.3 g 3-methylvaleryl chloride in 30 ml. benzene was added dropwise with stirring a mixture of 5 g beta-cyclogeranoil and 7.1 g triethylamine in 30 ml. benzene. The resulting suspension was stirred at room temperature overnight and then treated with 50 ml. of water. The layers were separated and the aqueous layer extracted twice with 30 ml. benzene. The combined organic extracts were washed successively with 50 ml. 3N HCl, 100 ml. saturated NaHCO$_3$ solution and 50 ml. H$_2$O. The organic layer was dried over MgSO$_4$ and concentrated to an oil. Distillation of the residual oil gave beta-cyclogeranyl 3-methylvalerate, bp 86°–90° C/0.2 mm.

The correct structural assignment was confirmed by the following spectroscopic data:

Infra-red (CCl$_4$): 1725, 1170 cm$^{-1}$

| 4.6 | (s, 2H) | —CH$_2$O |
| 1.68 | (s, 3H) | =C—CH$_3$ |
| 1.0 | (s, 6H) | CH$_3$ \ / CH$_3$ |
| 0.9–2.4 (broad) methyl and methylene protons | | |

Mass Spectrum: m/e 154, 136, 121, 107, 93

The aroma of the compound prepared as described in Example 9 has been described by a panel of experts as being sour and valerian resembling aged bleu cheese.

EXAMPLE 10

Alpha-cyclogeraniol

To a suspension of 1.25 g NaBH$_4$ in 50 ml. 95% ethanol cooled in an ice bath was added dropwise with stirring 5.0 g alpha-cyclocitral which had been prepared as described in Example 1. When the addition was complete, the ice bath was removed and water was added to dissolve any remaining solids. The reaction mixture was then stirred overnight at room temperature. The solvent was removed at reduced pressure and the residue taken up in ether, washed with 1 N acetic acid, dilute sodium bicarbonate and water. The ether extract was dried over sodium sulfate and concentrated to give 3.6 g alpha-cyclogeraniol as a colorless oil of 95% purity by gas chromatographic analysis.

The correct structural assignment was confirmed by the following spectroscopic data:

Infra-red (CCl$_4$): 3630, 3570, 1070 cm$^{-1}$
Proton Magnetic Resonance (CCl$_4$):

| 3.68 | (d, 2H, J=4H$_2$) | —CH$_2$O— |
| 1.7 | (s, 3H) | =C—CH$_3$ |
| 1.0 | (s, 3H) | CH$_3$ \ / CH$_3$ |
| 0.9 | (s, 3H) | |
| 5.53 | (broad, 1H) | =C—H |
| 1.0–2.0 (broad) ring methylenes | | |

Mass Spectrum: m/e 154 (M$^+$), 123, 121, 81, 69

The aroma of the compound prepared as described in Example 10 has been described by a panel of experts as reminiscent of menthol and camphor.

Upon application of the compound prepared as described in Example 10 to a blend of cigarette tobaccos at a level of 25 ppm, a panel of experts found the cigarette smoke to be sweeter and smoother than an untreated control cigarette.

EXAMPLE 11

Alpha-cyclogeraniol methyl ether

To a suspension of 0.41 g sodium hydride in 25 ml dimethoxyethane (DME) was added dropwise with magnetic stirring a solution of 3.0 g alpha-cyclogeraniol, prepared as described in Example 10, in 20 ml DME. The suspension was stirred vigorously for 1 hr. at room temperature. Then a solution of 3.04 g methyl iodide in 10 ml DME was added dropwise and the resulting suspension was heated under reflux overnight.

An aliquot was removed and worked-up; gas chromatographic analysis showed only 50% reaction had occurred. Accordingly, to the reaction mixture was added by syringe 4.3 ml of 2.3 M methyl lithium solution and after a few minutes 1.38 g methyl iodide. The reaction mixture was heated under reflux for 2 hrs. and cooled, filtered and concentrated to a paste. The paste was taken up in 75 ml ether, washed with an equal volume of water, the layers separated and the organic layer dried over sodium sulfate. The extract was filtered and concentrated at reduced pressure to give 2.3 g of alpha-cyclogeraniol methyl ether as a pale yellow oil.

The correct structural assignment was confirmed by the following spectroscopic data:

Infra-red (CCl$_4$): 1115, 865 cm$^{-1}$
Proton Magnetic Resonance (CCl$_4$):

| 5.4 | (broad singlet, 1H) | =C—H |
| 3.2–3.4 | (multiplet, 2H) | —CH$_2$—O |
| 1.65 | (t, 3H) J=2H$_2$ | =C—CH$_3$ |
| 0.82 | (s, 3H) | CH$_3$ \ / CH$_3$ |
| 0.88 | (s, 3H) | |
| 0.75–2.0 (broad) ring protons | | |

Mass Spectrum: m/e 168 (M$^+$), 136, 123, 93, 81

The aroma of the compound prepared as described in Example 11 has been described by a panel of experts as resembling camphor and menthol with woody terpene undertones.

EXAMPLE 12

Beta-cyclogeranyl thiomethyl ether

Beta-cyclogeranyl bromide was prepared according to the literature method described in Example 5 and was used without purification. The crude beta-cyclogeranyl bromide (13.6 g, 0.065 mole) was added dropwise with stirring to an equimolar quantity of sodium methylthiolate in 100 ml anhydrous methanol. The reaction mixture was heated under reflux overnight and then concentrated by distillation at atmospheric pressure. The residue was treated with 100 ml H$_2$O and the aqueous suspension extracted twice with 50 ml portions of ether. The combined ether extracts were washed once with 50 ml H$_2$O and dried over Na$_2$SO$_4$. The ether was removed at reduced pressure and the residual yellow oil was distilled to give beta-cyclogeranyl thiomethyl ether, bp 51° C/0.1 mm.

The correct structural assignment was confirmed by the following spectroscopic data:

Infra-red ($CCl_4$): 1360, 1235 cm$^{-1}$
Proton Magnetic Resonance ($CCl_4$):

| 3.08 | (s, 2H) | $-CH_2S$ |
| 2.0 | (s, 3H) | $-SCH_3$ |
| 1.65 | (s, 3H) | $=CH_2$ |
| 1.05 | (s, 6H) | $CH_3$ / $CH_3$ |

1.2–2.0 (broad) ring methylenes

Upon application of the compound prepared as described in this Example to a blend of cigarette tobaccos, at a level of 30 ppm, a panel of experts found the cigarette smoke to be smoother and more bland than an untreated control cigarette.

EXAMPLE 13

Beta-cyclogeranyl thiobutyl ether

Beta-cyclogeranyl bromide was prepared according to the literature method described in Example 5 and was used without purification. The crude beta-cyclogeranyl bromide (6.9 g. 0.032 mole) was added dropwise with stirring to an equimolar quantity of sodium butanethiolate in 125 ml anhydrous methanol. The reaction mixture was heated under reflux overnight and then concentrated by distillation at atmospheric pressure. The residue was treated with 100 ml $H_2O$ and 100 ml ether, the layers separated and the ether layer washed once with 50 ml $H_2O$. The organic layer was dried over $Na_2SO_4$ and concentrated at reduced pressure to give 6.0 g of an oil. Distillation of the oil gave beta-cyclogeranyl thiobutyl ether, bp 82°–95° C/0.1 mm.

The correct structural assignment was confirmed by the following spectroscopic data:

Infra-red ($CCl_4$): 1360 cm$^{-1}$
Proton Magnetic Resonance ($CCl_4$):

| 3.08 | (s,2H) | $-CH_2S$ |
| 1.65 | (s,3H) | $=C-CH_3$ |
| 1.0 | (s,6H) | $CH_3$ / $CH_3$ |
| 2.4 | (t,2H) | $-SCH_2-$ |

0.8–2.0 (broad) methylene protons

Mass Spectrum: m/e 226 (M$^+$), 137, 136, 121, 95

The aroma of the compound prepared as described in Example 13 has been described by a panel of experts as sulfur-like with woody notes.

Upon application of the compound prepared as described in Example 13 to a blend of cigarette tobaccos at a level of 30 ppm, a panel of experts found the cigarette smoke to be smoother and more bland than an untreated control cigarette.

In several modifications one or more of the compounds of this invention were admixed with other synthetic and natural flavorants and the mixtures applied to tobacco at appropriate levels. The treated tobacco was then manufactured into cigarettes in a conventional manner. A panel of flavor experts found that in general the compounds of the present invention produce a softening effect on the overall aroma of the cigarette smoke accompanied with increased sweetness and reduced harshness. In addition to effecting an improvement in the smoking quality of the products, the additives of the present invention produced mouth-wetting effects and usually a pleasant aftertaste.

It should be appreciated that in the art of flavor blending a variety of effects are possible from a flavorant depending on the amounts of flavorant used and on the nature of the substrate. The amounts of additive used in most of our modifications varied from 0.0005 percent to 0.0125 percent and the substrate was a commercial blend of tobacco containing added sugars, humectants and in some instances other flavorants.

It will be appreciated that while several embodiments of this invention are shown above, the invention is not to be limited thereto, since many modifications can be made by those skilled in the art without departing from the spirit and scope of the invention as set forth in the appended claims:

What is claimed is:

1. A method for improving the flavor of tobacco which comprises adding thereto an amount sufficient to alter the flavor of the tobacco of at least one compound of the following formulas:

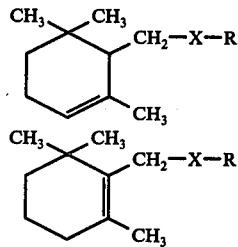

wherein X in both Formulas I and II above is oxygen or sulfur and R is selected from the group of hydrogen; alkyl having from 1 to 10 carbon atoms in the alkyl chain; cycloaliphatic; aryl; araalkyl; or acyl having from 1 to 9 carbon atoms in the acyl chain.

2. The method of claim 1 wherein the amount of said compound added to the tobacco is from about 0.0001 to about 0.1 percent by weight of the tobacco.

3. The method of claim 2, wherein X is oxygen.

4. The method of claim 3 wherein the amount of the compound added to the tobacco is from about 0.0001 to about 0.01 percent by weight of the tobacco. 0001

5. The method of claim 3 wherein R is an alkyl group having from 1 to 6 carbon atoms in the alkyl chain.

6. The method of claim 5 wherein R is methyl.

7. The method of claim 5 wherein R is iso-propyl.

8. The method of claim 5 wherein R is butyl.

9. The method of claim 5 wherein R is hexyl.

10. The method of claim 3 wherein R is hydrogen.

11. The method of claim 3 wherein R is an acyl residue of an aliphatic or aromatic mono-carboxylic acid having from 1 to 9 carbon atoms in the acyl chain.

12. The method of claim 11 wherein R has from 1 to 6 carbon atoms in the acyl chain.

13. The method of claim 12 wherein R is the acyl residue of acetic acid.

14. The method of claim 12 wherein R is the acyl residue of propionic acid.

15. The method of claim 12 wherein R is the acyl residue of valeric acid.

16. The method of claim 12 wherein R is the acyl residue of 3-methyl valeric acid.

17. The method of claim 2 wherein X is sulfur.

18. The method of claim 17 wherein R is an alkyl group having from 1 to 6 carbon atoms in the alkyl chain.

19. The method of claim 18 wherein R is methyl.

20. The method of claim 18 wherein R is butyl.

21. A tobacco or tobacco product having added thereto aboit 0.0001 to about 0.1 weight percent, based on the weight of the tobacco, of at least one compound having one of the following formulas:

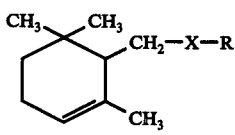  I

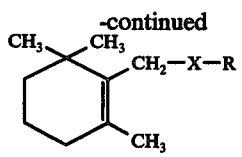  II wherein X in both Formulas I and II above is oxygen or sulfur and R is selected from the group of hydrogen; alkyl having from 1 to 10 carbon atoms in the alkyl chain; cycloaliphatic; aryl; araalky; or acyl having from 1 to 9 carbon atoms in the acyl chain.

22. The product of claim 21 wherein the compound is selected from the group consisting of beta-cyclogeraniol, beta-cyclogeranoil methyl ether, beta-cyclogeraniol isopropyl ether, beta-cyclogeraniol butyl ether, betacyclogeraniol hexyl ether, beta-cyclogeraniol acetate, beta-cyclogeraniol propionate, beta-cyclogeraniol valerate, beta-cyclogeraniol 3-methyl valerate, alpha-cyclogeraniol, alpha-cyclogeraniol methyl ether, beta-cyclogeranyl thiomethyl ether, and beta-cyclogeranyl thiobutyl ether.

23. The product of claim 22 wherein the compound is beta-cyclogeraniol.

24. The product of claim 22, wherein the compound is beta-cyclogeranyl acetate.